(12) United States Patent
Dreyer et al.

(10) Patent No.: US 7,799,790 B2
(45) Date of Patent: *Sep. 21, 2010

(54) AMORPHOUS ARIPIPRAZOLE AND PROCESS FOR THE PREPARATION THEREOF

(75) Inventors: Katja Dreyer, Hamburg (DE); Uwe Loeffler, Tornesch (DE); Klaus Glaenzer, Hamburg (DE)

(73) Assignee: Helm AG, Hamburg (DE)

( * ) Notice: Subject to any disclaimer, the term of this patent is extended or adjusted under 35 U.S.C. 154(b) by 127 days.

This patent is subject to a terminal disclaimer.

(21) Appl. No.: 12/131,618

(22) Filed: Jun. 2, 2008

(65) Prior Publication Data

US 2008/0280921 A1    Nov. 13, 2008

Related U.S. Application Data

(63) Continuation-in-part of application No. 11/463,062, filed on Aug. 8, 2006.

(30) Foreign Application Priority Data

Jul. 20, 2006  (EP) .................................. 06117595
Jan. 23, 2008  (EP) .................................. 08150576

(51) Int. Cl.
*A61K 31/497*  (2006.01)
*C07D 401/12*  (2006.01)
(52) U.S. Cl. .................. 514/253.07; 544/363
(58) Field of Classification Search ............ 514/253.07; 544/363
See application file for complete search history.

(56) References Cited

U.S. PATENT DOCUMENTS

| 4,734,416 | A | 3/1988 | Bano et al. |
|---|---|---|---|
| 5,006,528 | A | 4/1991 | Oshiro et al. |
| 2004/0170672 | A1 | 9/2004 | Selzer |
| 2004/0247870 | A1 | 12/2004 | Brown et al. |
| 2005/0245539 | A1 | 11/2005 | Mendla et al. |
| 2005/0272742 | A1 | 12/2005 | Worthen et al. |
| 2008/0020038 | A1* | 1/2008 | Stritzke et al. .............. 424/468 |
| 2008/0280921 | A1* | 11/2008 | Dreyer et al. .......... 514/253.07 |

FOREIGN PATENT DOCUMENTS

| EP | 1 398 040 | 3/2004 |
|---|---|---|
| EP | 1 419 776 | 5/2004 |
| EP | 1 330 249 | 4/2006 |
| EP | 1 880 714 | 1/2008 |
| WO | WO 03/026659 | 4/2003 |
| WO | WO 2004/083183 | 9/2004 |
| WO | WO 2004/106322 | 12/2004 |
| WO | WO 2005/009990 | 2/2005 |
| WO | WO 2005/016262 | 2/2005 |
| WO | WO 2005/058835 | 6/2005 |
| WO | WO 2006/053781 | 5/2006 |
| WO | WO 2006/079549 | 8/2006 |
| WO | WO 2007/073389 | 6/2007 |
| WO | WO 2008/020820 | 2/2008 |

OTHER PUBLICATIONS

Aoki et al., "Study on Crystal Transformation of Aripiprazol," The Proceedings of the 4th Japanese-Korea Symposium on Separation Technology, CR.119 (Oct. 6-8, 1996) pp. 937-940.
www.fda.gov/cder/foi/nda/2002/21-436, Abilify_biophamr_P2.
FDA, Enforcement Report, Aug. 25, 2004 and Jul. 6, 2005.
Office Action issued Jan. 25, 2010 in U.S. Appl. No. 11/463,062.

* cited by examiner

*Primary Examiner*—James O Wilson
*Assistant Examiner*—Ebenezer Sackey
(74) *Attorney, Agent, or Firm*—Swanson & Bratschun, L.L.C (57) ABSTRACT

Morphologically stabilized amorphous aripiprazole and process for preparing the same.

29 Claims, 5 Drawing Sheets

AMORPHOUS ARIPIPRAZOLE AND PROCESS FOR THE PREPARATION THEREOF

RELATED APPLICATIONS

This application is a continuation-in-part of U.S. application Ser. No. 11/463,062, filed Aug. 8, 2006, which claims priority to European Application Serial No. 06117595.6, filed Jul. 20, 2006, each of which is entitled "Amorphous Aripiprazole and Process for the Preparation thereof." This application also claims priority to European Patent Application Serial No. EP 08150576.0, filed Jan. 23, 2008. Each of these applications is specifically incorporated herein by reference in its entirety.

FIELD OF INVENTION

The present invention relates to oral formulations containing morphologically stabilized amorphous aripiprazole which has enhanced dissolution abilities. Another aspect of the invention relates to pharmaceutical dosage forms containing stabilized amorphous aripiprazole which can be used for instance for the treatment of schizophrenia and psychotic disorders.

BACKGROUND OF THE INVENTION

Aripiprazole, 7-{4-[4-(2,3-dichlorophenyl)-1-piperazinyl]-butoxy}-3,4-dihydro carbostyril or 7-{4-[4-(2,3-dichlorophenyl)-1-piperazinyl]-butoxy}-3,4-dihydro-2(1H)-quinolinone, is an atypical antipsychotic agent useful for the treatment of schizophrenia. Schizophrenia is a common type of psychosis characterized by delusions, hallucinations and extensive withdrawal from others. The preparation of aripiprazole and other carbostyril derivatives is described in U.S. Pat. No. 4,734,416 and U.S. Pat. No. 5,006,528. These processes do not result in the formation of well defined, reproducible forms of aripiprazole.

Aripiprazole is known in several polymorphic forms. The Proceedings of the 4$^{th}$ Japanese-Korean Symposium on Separation Technology (Oct. 6-8, 1996) state that, aripiprazole anhydride crystals exist as anhydrous type-I crystals (conventional anhydride), anhydrous type-II crystals, and type III hydrate (conventional hydrate); the type-I crystals of aripiprazole anhydride (conventional anhydride) can be prepared by recrystallization from an ethanol solution of aripiprazole, or by heating aripiprazole hydrate at 80° C. The type-II crystals of aripiprazole anhydride can be prepared by heating conventional anhydride at 130° to 140° C. for 15 hours. Type III crystals (conventional hydrate) were recrystallized from alcoholic solvent containing up to 20% (v/v) of water.

The hygroscopicity of the conventional anhydride crystals makes them difficult to handle since costly and burdensome measures must be taken in order to ensure that they are not exposed to moisture during preparation and formulation. When exposed to moisture, the conventional anhydrous forms of aripiprazole absorb water and convert to hydrous forms such as the monohydrate. The hydrous forms of aripiprazole have the disadvantage of being less soluble than the anhydrous forms. Moreover, variation in the amount of hydrous versus anhydrous aripiprazole from batch to batch makes it difficult to meet the specifications set by drug regulatory authorities. Furthermore, the solubility of aripiprazole is pH-dependent which influence the dissolution rate.

Numerous attempts have been made to overcome these disadvantages.

To ensure appropriate dissolution of poorly soluble drugs the drugs are commonly used in particle sizes smaller 50 µm. The small particle sizes are usually obtained by energy involved processes like extensive milling, micronization or grinding.

EP 1 330 249 and EP 1 419 776 disclose polymorphic modifications of aripiprazole which are said to have reduced hygroscopicity, such as anhydride B. Anhydride B can be obtained by milling conventional hydrate to provide intermediary hydrate A (particle size less 50 µm), which is converted to aripiprazole form B by heating to 90-125° C. for 3 to 50 hours. Anhydride B can be converted to a glassy state by heating to about 170° C. and cooling to room temperature. The glassy form of aripiprazole anhydride forms aripiprazole anhydride crystals of form G upon storing. In addition to hydrate A and anhydrides B and G aripiprazole anhydride crystals of forms C to F are described.

EP 1 606 262 discloses two crystalline forms of aripiprazole and four crystalline forms of aripiprazole hydrochloride which are said to be stable over the time and to be reproducible.

WO 2005/009990 discloses crystalline forms of aripiprazole, aripiprazole methanolate and aripiprazole ethylene dichloride solvate. These crystalline forms of aripiprazole are said to be non hygroscopic and to have no tendency to convert to other forms.

WO 2004/106322 describes the preparation of polymorphic forms II, III and IV of aripiprazole. Form II is described as having a melting point of 133 to 135° C., Form III of 122 to 125° C. and Form IV of 146 to 149° C.

WO 2005/058835 discloses anhydrous aripiprazole crystalline forms I, II, VI, VIII, X, XI, XII, XIV, XIX, XX and methods for preparing the same. These forms of aripiprazole are said to be non-hygroscopic and to maintain compound stability during storage. They can be prepared directly by slurrying without heating a preexisting hydrate crystal form.

EP 1 398 040 discloses a medicinal composition prepared by dissolving or dispersing a drug like aripiprazole and a pH-independent, water-insoluble polymer in a wax-like or glycerine ester or fatty acid like low-melting-point substance or dispersing a drug in a mixture of both.

None of the above forms of aripiprazole is completely satisfactory. For instance, during approval of aripiprazole tablets in Europe and the United States the 20- and 30-mg tablets had to be redesigned because they exhibited less than complete and slower dissolution than other aripiprazole tablet strengths at pH 1.2 (see www.fda.gov/cder/foi/nda/2002/21-436_Abilify_biopharmr_P2). In spite of this effort, the manufacturer had to recall several batches of tablets due to dissolution failure (FDA, Enforcement Report 25 Aug. 2004 and 6 Jul. 2005).

As can be seen from the above, there is a strong need for aripiprazole having a stable morphology and showing defined and stable dissolution rates. Moreover, due to the poor performance of the marketed products, the development of a stable and reproducibly bioavailable formulation of aripiprazole tablets is highly desired. None of the above mentioned forms or formulations have demonstrated sufficient bioavailability.

It is an object of the invention to provide aripiprazole in morphologically stable form with good solubility in aqueous systems which can be easily prepared.

SUMMARY OF THE INVENTION

The present invention relates to oral formulations containing morphologically stable amorphous aripiprazole which has enhanced dissolution abilities.

The invention provides aripiprazole or a pharmaceutically acceptable salt thereof in stabilized amorphous form. The preparation of the amorphous aripiprazole of the present invention does not require grinding, the use of water-free conditions or the use of special polymorphic forms as starting materials. The dissolution rate of the stabilized amorphous aripiprazole of the present invention is not influenced by the formation of hydrates during storage and does therefore not require protection against moisture during storage.

Another aspect of the invention relates to pharmaceutical compositions comprising morphologically stabilized amorphous aripiprazole which can be used e.g. for the treatment of schizophrenia and psychotic disorders.

A further aspect of the invention relates to a process for preparing morphologically stabilized amorphous aripiprazole.

The above objects are achieved by pharmaceutical compositions comprising amorphous aripiprazole or a pharmaceutically acceptable salt thereof and at least one stabilizing agent.

DETAILED DESCRIPTION OF THE INVENTION

The present invention for the first time provides amorphous aripiprazole or a pharmaceutically acceptable salt thereof which is morphologically stable as well as pharmaceutical composition comprising morphologically stable amorphous aripiprazole or a salt thereof. The pharmaceutical compositions of the present invention preferably contain at least one stabilizing agent, i.e. an agent which stabilizes aripiprazole in its amorphous form and prevents crystallization thereof. In the following, these mixtures of amorphous aripiprazole with at least one stabilizing agent will also be referred to as morphologically stabilized amorphous aripiprazole or stabilized amorphous aripiprazole.

The morphologically stabilized amorphous aripiprazole of the present invention may comprise minor amounts of crystalline aripiprazole. Preferably the amorphous aripiprazole of the invention comprises less than 20% by weight of crystalline aripiprazole, more preferably less than 10% by weight, even more preferably less than 5% by weight, e.g. less than 2% by weight, based on the total amount of aripiprazole. Most preferably the stabilized aripiprazole of the present invention comprises substantially no crystalline aripiprazole.

The stabilized aripiprazole of the present invention preferably comprises aripiprazole and stabilizing agent in a weight ratio of 1:20 to 5:1. According to one preferred embodiment of the present invention the compositions comprise 4.8 to 83.3 wt.-% of aripiprazole, based on the total weight of the composition. It is further preferred that the compositions comprise 3.8 to 66.7 wt.-% of amorphous aripiprazole, i.e. the amount of crystalline aripiprazole is within a range of 0 to 16.6 wt.-%, based on the total weight of the composition.

It was surprisingly found that the stabilized amorphous aripiprazole of the present invention is better soluble in aqueous systems than the known crystalline forms of aripiprazole. It can be stored for prolonged time periods without changing its morphological structure, i.e. without crystallization. It was particularly surprising to find that the storage stability is not impaired by the presence of minor amounts of crystalline aripiprazole which would have been expected to induce crystallization of the whole material. Even after storage the morphologically stabilized amorphous aripiprazole of the present invention shows no significant change in the dissolution abilities.

Surprisingly, a pharmaceutical formulation containing morphologically stabilized aripiprazole according to the invention shows advantageous biopharmaceutical properties. Preferably, an oral formulation containing stabilized amorphous aripiprazole according to the invention can be characterized by a bioavailability with an average $c_{max}$ larger than 25 ng/ml of aripiprazole, an average $t_{max}$ below 4 hours and an average $AUC_\infty$ larger than 1500 ng·h/ml.

As a consequence of the observed bioavailability in healthy volunteers, the invention therefore provides a pharmaceutical composition comprising morphologically stabilized amorphous aripiprazole which can be used e.g. for the treatment of schizophrenia and psychotic disorders.

According to the present invention aripiprazole is stabilized in amorphous form by admixture with at least one stabilizing agent which is selected from the group consisting of embedding materials and/or solubilizers.

Preferred stabilizing agents are polyvinyl pyrrolidone, polymethacrylate, polyvinyl acetate phthalate, alkyl cellulose, hydroxyl alkyl cellulose, polyethylene glycol, polyethylene castor oil, polyethylene glycol sorbitan fatty acid, polyethylene polypropylene glycol, polyethylene oxide, polyoxyethylene alkyl ether, polyoxyethylene stearate, and derivatives of these substances, and mixtures thereof.

More preferred stabilizing agents are selected from polyvinyl pyrrolidone, polymethacrylate, polyethylene glycol, polyethylene castor oil, polyoxyethylene hydrogenated castor oil, polyethylene glycol sorbitan fatty acid, polyoxyethylene stearate, and mixtures thereof.

Particularly preferred stabilizing agents are selected from polyethylene glycol having an average molecular weight within the range of 190 to 10,000, polyethylene oxide sorbitan mono-oleate, polyoxyl 40 hydrogenated castor oil, polyoxyl 35 castor oil, polyethylene glycol-15-hydroxystearate, pH-dependent water-soluble polymethacrylates, such as dimethyl aminoethyl methacrylate copolymer, and vinyl pyrrolidone-vinyl acetate copolymer.

The most preferred stabilizing agents are selected from polyethylene glycol having an average molecular weight within the range of 190 to 10,000, pH-dependent water-soluble polymethacrylates, such as dimethyl aminoethyl methacrylate copolymer, and vinyl pyrrolidone-vinyl acetate copolymer.

The stabilizing agent(s) can further be used in combination with an acidic compound, preferably an organic acid, such as tartaric acid or citric acid.

The term "pH-dependent water-soluble polymethacrylate" as used herein refers to a polymethacrylate wherein solubility in aqueous solution is dependent from the pH of said solution. Polymethacrylates which are soluble in aqueous solution up to pH 5.0 are preferred. Particularly preferred pH-dependent water-soluble polymethacrylates are methacrylate copolymers having tertiary amino groups, such as dimethyl aminoethyl methacrylate copolymer, e.g. Eudragit E 100 or Eudragit EPO.

The stabilised amorphous aripiprazole of the present invention may comprise one or more stabilising agents. The use of 1 to 5 and in particular 2 to 3 stabilising agents is preferred.

If only one stabilizing agent is used, the stabilizing agent is preferably selected from polyethylene glycol sorbitan fatty acid, polyoxyethylene hydrogenated castor oil, polyoxyethylene castor oil, polyethylene glycol stearate, polymethacrylate, and derivatives thereof. More preferably the stabilizing agent is selected from polyethylene oxide sorbitan monooleate, polyoxyl 40 hydrogenated castor oil, polyoxyl 35 castor oil, polyethylene glycol-15-hydroxystearate, and pH-dependent water-soluble polymethacrylates, such as dimethyl aminoethyl methacrylate copolymers. Most preferably the stabilizing agent is selected from polyethylene glycol having an average molecular weight within the range of 190 to 10,000 and pH-dependent water-soluble polymethacrylates, such as dimethyl aminoethyl methacrylate copoylmers.

Compositions comprising at least two different stabilizing agents are preferred. If two different stabilizing agents are used the stabilizing agents are preferably selected from embedding materials and/or solubilizers. More preferably at least one stabilizing agent is selected from the group of embedding materials and at least one stabilizing agent is selected from the group of solubilizers.

According to the invention embedding materials are understood to be a kind of matrix or carrier material. Preferable embedding materials are physiologically acceptable polymers or copolymers based on vinyl compounds. The polyvinyl compounds may optionally be functionalized. They are preferably substituted by pyrrolidone, alkyl, ether, phenyl, amino, alkyl amino, dialkyl amino, ammonium, carboxy acid ester, carboxy acid, carboxy acid amide and/or acetate groups. Additionally, embedding materials can be selected from alkyl cellulose or hydroxyl alkyl cellulose.

According to the invention solubilizers are understood to be surfactants, or solubilizing, solubility enhancing agents or cosolvents for aripiprazole or a salt thereof. Preferred solubilizers are physiologically acceptable polymers or copolymers of ethylene glycol. The polyethylene compounds may optionally be functionalized. They are preferably substituted by substituents selected from fatty acids, fatty acid esters, fatty acid amides, castor oils, ethers, higher alcohols, alkyl, phenyl, amino, alkyl amino, dialkyl amino, or polyalcohol groups.

The first stabilizing agent is preferably selected from the group of embedding materials consisting of polyvinyl pyrrolidone, polymethacrylates, polyvinyl acetate phthalate, alkyl cellulose, hydroxyl alkyl cellulose, derivatives of these substances, and mixtures thereof.

More preferably the first stabilizing agent is selected from polyvinyl pyrrolidone, vinylpyrrolidone-vinylacetate copolymer, methacrylic acid copolymer, amino alkyl methacrylate copolymer, methacrylic acid ester copolymer, ammonium alkyl methacrylate copolymer, methyl cellulose, ethyl cellulose, hydroxypropylmethyl cellulose, and mixtures thereof.

Particularly preferably the first stabilizing agent is selected from vinyl pyrrolidone-vinyl acetate copolymer, pH-dependent water-soluble polymethacrylates, such as dimethyl aminoethyl methacrylate copolymers, and mixtures thereof.

Most preferably the first stabilizing agent is selected from pH-dependent water-soluble polymethacrylates, such as dimethyl aminoethyl methacrylate copolymer.

According to a particularly preferred embodiment, the first stabilizing agent is a pH-dependent water-soluble polymethacrylate, such as a dimethyl aminoethyl methacrylate copolymer, in combination with an acidic compound, preferably an organic acid, such as tartaric acid or citric acid. Preferably the pH-dependent water-soluble polymethacrylate and the acidic compound are used in a weight ratio of 50:1 to 10:1, more preferably 25:1 to 15:1.

The second stabilizing agent is preferably selected from solubilizers. Preferably the stabilizing agents are selected from compounds which cause a lowering of the melting point of an embedding compound and additionally have the property of a solubilizer. Preferably the second stabilizing agent is selected from of polyethylene glycol, polyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

More preferably the second stabilizing agent is selected from polyethylene glycol, polyethylene castor oil, polyoxyethylene hydrogenated castor oil, polyoxyethylene hydroxy stearate, polyethylene glycol sorbitan mono fatty acid, derivatives of these substances, and mixtures thereof.

Particularly preferably the second stabilizing agent is selected from polyethylene glycol having an average molecular weight within the range of 190 to 10,000, polyoxyl 35 castor oil, polyoxyl 40 hydrogenated castor oil, polyethylene glycol-15-hydroxystearate, polyoxyethylene sorbitan monooleate, and mixtures thereof.

Most preferably the second stabilizing agent is selected from polyethylene glycol having an average molecular weight within the range of 190 to 10,000.

The stabilized amorphous aripiprazole of the present invention preferably comprises 15 to 95 wt.-%, more preferably 25 to 93 wt.-% and most preferably 45 to 91 wt.-% of one or more stabilizing agents, based on the total weight of aripiprazole and stabilizing agent(s).

In addition to the aripiprazole or a salt thereof and the one or more stabilizing agents the compositions of the invention comprises one or more pharmaceutically acceptable excipients.

The pharmaceutical compositions of the present invention have preferably the form of oral dosage forms, such as granules, pellets, capsules, and in particular tablets, such as flash-melt tablets, oral dispersible tablets, sustained release tablets and immediate release tablets.

The pharmaceutical compositions of the present invention preferably comprise:

1 to 99.5 wt.-%, more preferably 5 to 75 wt.-% and most preferably 20 to 65 wt.-% of stabilized amorphous aripiprazole, and 0.05 to 99 wt.-%, more preferably 25 to 95 wt.-% and most preferably 35 to 80 wt.-% of further excipients.

The compositions preferably contain 1 to 200 mg, more preferably 1 to 100 mg and most preferably 1 to 30 mg of aripiprazole per unit dose.

The known pharmaceutical excipients can be used to prepare the pharmaceutical formulations of the invention, such as fillers, lubricants, disintegration aids, wetting agents, agents to improve the flow behavior, antioxidants, flavors, taste masking agents, pigments, dyes, lubricants and other additives, e.g. as disclosed in "Die Tablette", W. A. Ritschel and A. Bauer-Brandl, 2$^{nd}$ ed., ECV-Edition Cantor publishers, 2002, the disclosure of which is incorporated herein by reference.

Preferred fillers are celluloses and cellulose derivatives, such as microcrystalline cellulose, native cellulose, hydroxypropyl cellulose, hydroxypropyl methyl cellulose, methyl cellulose, sugars, such as lactose, fructose, saccharose, glucose, maltose, sugar alcohols, such as lactitol, mannitol, sorbitol, xylitol, inorganic fillers, such as calcium phosphates and calcium sulfates, and starches, such as corn starch, potato starch, wheat starch, dextrins, and pregelatinized starches. Mannitol is particularly preferred.

Preferred disintegration aids are crosslinked polyvinyl pyrrolidone, starch and modified starches. Crosslinked polyvinyl pyrrolidone is particularly preferred.

Preferred flavors are vanilla, cherry, lemon, and cacao. Preferred taste masking agents are ascorbic acid, citric acid, tartaric acid, apple acid and polymethacrylate.

Preferred lubricants are fatty acids, such as stearic acid, fumaric acid, and salts thereof.

Preferred sweetening agents are acesulfame potassium, cyclamate and its salts, aspartame, saccharin and its salts or mixtures thereof.

The tablets can be coated or uncoated. Sugar-coated tablets, gelatin-coated tablets, enteric coated tablets and film coated tablets are preferred as coated tablets. Furthermore, the tablets can be double tablets or multilayered tablets.

The pharmaceutical compositions of the present invention preferably have the form of immediate release tablets or orodispersible tablets.

Immediate release tablet preferably comprise:

1 to 99 wt.-%, preferably 25 to 70 wt.-% and more preferably 30 to 50 wt.-% of morphologically stabilized amorphous aripiprazole, 0 to 50 wt.-%, preferably 0.5 to 50 wt.-%, more preferably 2 to 25 wt.-% and most preferably 4 to 15 wt.-% disintegration aids, 0 to 90 wt.-%, preferably 0.5 to 90 wt.-%, more preferably 10 to 60 wt.-% and most preferably 25 to 50 wt.-% filler, 0 to 5 wt.-% flavor, and 0 to 10 wt.-%, preferably 0.1 to 10 wt.-%, more preferably 0.3 to 5 wt.-% and most preferably 0.5 to 3 wt.-% lubricant.

Orodispersible tablets preferably comprise:

1 to 99 wt.-%, preferably 3 to 50 wt.-% and more preferably 5 to 40 wt.-% morphologically stabilized amorphous aripiprazole, 0 to 10 wt.-%, preferably 0.3 to 6 wt.-% and more preferably 0.5 to 2 wt.-% taste masking agent, 0 to 90 wt.-%, preferably 0.5 to 90 wt.-%, more preferably 40 to 90 wt.-% and most preferably 70 to 85 wt.-% filler, 0 to 50 wt.-%, preferably 0.5 to 50 wt.-% disintegration aids, 0 to 5 wt.-%, preferably 0.1 to 5 wt.-%, more preferably 0.2 to 5 wt.-% and most preferably 0.3 to 3 wt.-% lubricant, and 0 to 5 wt.-% flavor.

The morphologically stabilized amorphous aripiprazole of the present invention can be prepared by mixing aripiprazole with a stabilizing agent or a mixture of stabilizing agents. Preferably two different stabilizing agents are used, as described above.

Preferably the aripiprazole is dissolved in stabilizing agent(s) at elevated temperature, preferably at a temperature within the range of 30 to 190° C., and then the solution is optionally cooled. If only one stabilizing agent is used for preparing morphologically stabilized amorphous aripiprazole the stabilizing agent is preferably selected from polyethylene glycol sorbitan fatty acid, such as polyethylene oxide sorbitan mono-oleate; polyoxyethylene hydrogenated castor oil, such as polyoxyl 40 hydrogenated castor oil; polyoxyethylene castor oil, such as polyoxyl 35 castor oil; polyethylene glycol stearate, such as polyethylene glycol-15-hydroxystearate; polymethacrylate, such as dimethyl aminoethyl methacrylate copolymer. A particularly preferred stabilizing agent is polyoxyl 35 castor oil. The most preferred stabilizing agent is a pH-dependent water-soluble polymethacrylate, such as a dimethyl aminoethyl methacrylate copolymer.

If only one stabilizing agent is used, the stabilizing agent and aripiprazole are preferably used in a weight ratio of 1:5 to 5:1, more preferred 1:1. The compounds are preferably mixed at a temperature within the range of 40 to 190° C., more preferably 50 to 90° C., most preferably 60° to 75° C.

According to a preferred embodiment of the invention, aripiprazole is dissolved in a mixture of at least two different stabilizing agents at elevated temperature and then the solution is optionally cooled. According to this embodiment of the invention the first stabilizing agents is preferably selected from polyvinyl pyrrolidone, polymethacrylate, polyvinyl acetate phthalate, alkyl cellulose, hydroxyalkyl cellulose, derivatives of these substances, and mixtures thereof.

Particularly preferably the first stabilizing agent is polyvinyl pyrrolidone, such as vinylpyrrolidone-vinyl acetate copolymer or a pH-dependent water-soluble polymethacrylate, such as dimethyl aminoethyl methacrylate copolymer. Most preferably the first stabilizing agent is a pH-dependent water-soluble polymethacrylate, such as a dimethyl aminoethyl methacrylate copolymer.

The second stabilizing agent is preferably selected from polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

Particularly preferably the second stabilizing agent is selected from polyethylene glycol with an average molecular weight from 190 to 10000, polyoxyl 35 castor oil, polyoxyl 40 hydrogenated castor oil, polyethylene glycol-15-hydroxystearate, polyoxyethylene sorbitan monooleate.

Most preferably the second stabilizing agent is selected from polyethylene glycol with an average molecular weight from 190 to 10000.

Particularly preferably a mixture of vinylpyrrolidone-vinyl acetate copolymer and polyethylene glycol having a molecular weight of about 6000 is used.

Most preferably a mixture of a pH-dependent water-soluble polymethacrylate, such as a dimethyl aminoethyl methacrylate copolymer, and polyethylene glycol with an average molecular weight from 190 to 10000, particularly about 2000 to 8000 is used.

The first stabilizing agent, the second stabilizing agent and aripiprazole are preferably used in a weight ratio of 10:10:1 to 0.5:0.5:1, more preferably 5:5:1 to 2:2:1.

The active ingredient and the stabilizing agent(s) are preferably mixed at a temperature within the range of 40 to 190° C., more preferably 100 to 180° C., most preferably 140° to 180° C. It is particularly preferred that the active ingredient and the stabilizing agent(s) are mixed and heated in an extruder, such as but not limited to a hot-melt-extruder, at a temperature within the range of 40 to 190° C., more preferably 100 to 180° C., most preferably 140° to 150° C., followed by extrusion of the mixture.

The first stabilizing agent and the second stabilizing agent are preferably used in a weight ratio of 10:1 to 1:10, more preferably 5:1 to 1:2, most preferably 1:1. Alternatively, the first stabilizing agent and the second stabilizing agent are used in a weight ratio of 4.9:1 to 4:1.

Aripiprazole is preferably used in an amount of 5 to 50 wt.-%, based on the total weight of aripiprazole and stabilizing agent(s).

According to a further preferred embodiment of the invention aripiprazole is first dissolved in an organic solvent at elevated temperature, followed by the addition of at least one stabilizing agent. Alternatively, the aripiprazole may be added to a solution of the stabilizing agent(s) in an organic solvent. The compounds are mixed until a solution is obtained and then the organic solvent is removed.

Preferred organic solvents are ethanol, ethyl acetate, methanol, isopropyl alcohol, isopropyl acetate, dichloro methane, toluene, chloroform, preferred ethanol, acetone and mixtures thereof.

If an organic solvent is used, it is preferred to use at least two different stabilizing agents, more preferably a first and a second stabilizing agent as defined above.

If organic solvent is used it is preferred to use a first stabilizing agent which is preferably selected from polyvinyl pyrrolidone, polymethacrylate, polyvinyl acetate phthalate, alkyl cellulose, hydroxyl alkyl cellulose, derivatives of these substances, and mixtures thereof.

Most preferably the first stabilizing agent is polyvinylpyrrolidone, such as vinylpyrrolidone-vinyl acetate copolymer, or a pH-dependent water-soluble polymethacrylate, such as a dimethyl aminoethyl methacrylate copolymer.

The second stabilizing agent is preferably selected from polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.

Particularly preferably the second stabilizing agent is selected from polyoxyl 35 castor oil and polyoxyl 40 hydrogenated castor oil.

Most preferably the second stabilizing agent is selected from polyethylene glycol with an average molecular weight from 190 to 10000.

According to the present invention it is particularly preferred to use a combination of polyoxyl 40 hydrogenated castor oil and vinylpyrrolidone-vinyl acetate copolymer, or a combination of polyoxyl 35 castor oil and vinylpyrrolidone-vinyl acetate copolymer as stabilizing agents. It is even more preferred to use a combination of polyethylene glycol with an average molecular weight from 190 to 10000, particularly about 2000 to 8000, and a pH-dependent water-soluble polymethacrylate, such as a dimethyl aminoethyl methacrylate copolymer, as stabilizing agents.

The first stabilizing agent, the second stabilizing agent and aripiprazole are preferably used in a weight ratio of 10:10:1 to 0.5:0.5:1, more preferably 4.5:4.5:1. The active ingredient, the organic solvent and the stabilizing agent(s) are preferably mixed at a temperature within the range of 40 to 120° C., more preferably 50 to 90° C., most preferably 60° to 75° C.

The first stabilizing agent and the second stabilizing agent are preferably used in a weight ratio of 10:1 to 1:10, more preferably 5:1 to 1:2, most preferably 1:1. Alternatively, the first stabilizing agent and the second stabilizing agent are used in a weight ratio of 4.9:1 to 4:1.

Aripiprazole is preferably used in an amount of 5 to 50 wt.-%, based on the total weight of aripiprazole and stabilizing agent(s).

To prepare morphologically stabilized amorphous aripiprazole any known polymorphic form, salt or solvate of aripiprazole can be used, for example conventional anhydride, conventional hydrate, type III, form A, form B, form I, form II, form III, form IV, VI, VIII, X, XI, XII, XIV, XIX, XX.

The preparation is not limited to anhydride polymorphic forms of aripiprazole. Aripiprazole of any particle size may be used. No previous grinding is necessary. Preferred salts of aripiprazole are the acid-addition salts, in particular the salts of hydrochloric acid, sulfuric acid, phosphoric acid, hydrobromic acid, oxalic acid, maleic acid, fumaric acid, malic acid, tartaric acid, citric acid, and benzoic acid.

The morphologically stabilized amorphous aripiprazole obtained by any of the above procedures can be used directly for the preparation of pharmaceutical compositions or may be first subjected to grinding, sieving, or milling.

Oral pharmaceutical formulations can be produced for instance by direct compression, dry-granulation, wet-granulation, preferably by melt extrusion, melt granulation or pelletization. Particularly, oral pharmaceutical formulations can be produced by direct compression of a dry mixture of the morphologically stabilized amorphous aripiprazole or pharmaceutically acceptable salt thereof and one or more pharmaceutically acceptable excipients, or by compression of a granulate manufactured from the morphologically stabilized amorphous aripiprazole or pharmaceutically acceptable salt thereof and one or more pharmaceutically acceptable excipients by wet-granulation.

Dissolution rates of the pharmaceutical compositions and formulations according to the invention can be determined according to USP (900 ml buffer pH 1.2, 37° C., 60 rpm).

Preferably, the pharmaceutical compositions and formulations according to the invention exhibit a dissolution profile wherein under the above conditions within 5 minutes at least 95 wt.-%, particularly at least 98 wt.-%, most preferably at least 99.5 wt.-% of aripiprazole are dissolved.

EXAMPLES

For the preparation of morphologically stabilized amorphous aripiprazole the conventional anhydride of aripiprazole prepared according to Example 1 of EP 0 367 141 A2 was used.

All X-ray diffraction measurements were performed in the transmission mode using the following conditions:
Cu-K$\alpha_1$-radiation ($\lambda$=1.54056 Å), U=40 kV, I=30 mA.
Primary Monochromator (curved Ge(111)).
Position Sensitive Detector, sample movement $\Delta\omega$.
Slits: 1 mm, 8 mm diameter.
Angle region: $2\theta$=3 to 35°, steps $\Delta 2\theta$=0.2° (0.02°), t=18 s/step Example 1

Preparation of Stabilized Amorphous Aripiprazole by Mixing the Active Ingredient with Two Stabilizing Agents (Macrogol 6000/Kollidon VA 64) in the Absence of Organic Solvent 10 g of polyethylene glycol (Macrogol 6000) and 10 g of polyvinyl pyrrolidone (Kollidon VA 64) were heated in a glass vessel to T≈150° C. to 180° C. At that temperature 4.98 g aripiprazole (Example 1) were added with stirring to obtain a homogeneous solution. Stirring was continued for an additional 10 min., the mixture was poured into a mortar and allowed to cool down to room temperature. X-ray diffraction measurement of the product resulted in the spectrum shown in FIG. 1.

Figure 1:
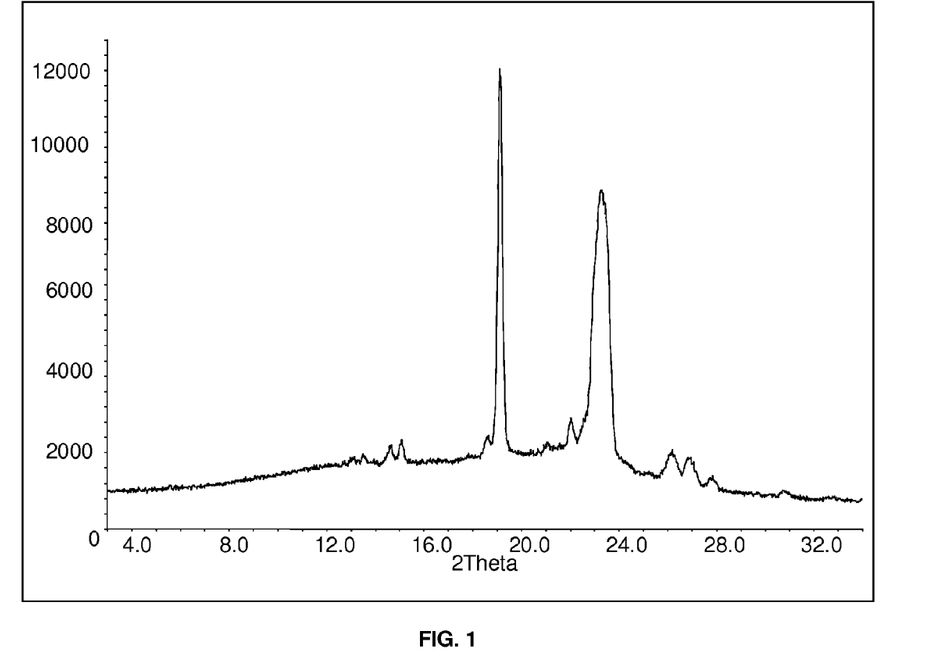
FIG. 1 shows the powder X-ray diffraction pattern of aripiprazole stabilized with polyethylene glycol (Macrogol 6000) and polyvinyl pyrrolidone (Kollidon VA 64) according to Example 1. The observed peaks are due to matrix only (compare FIG. 2).
Figure 2:
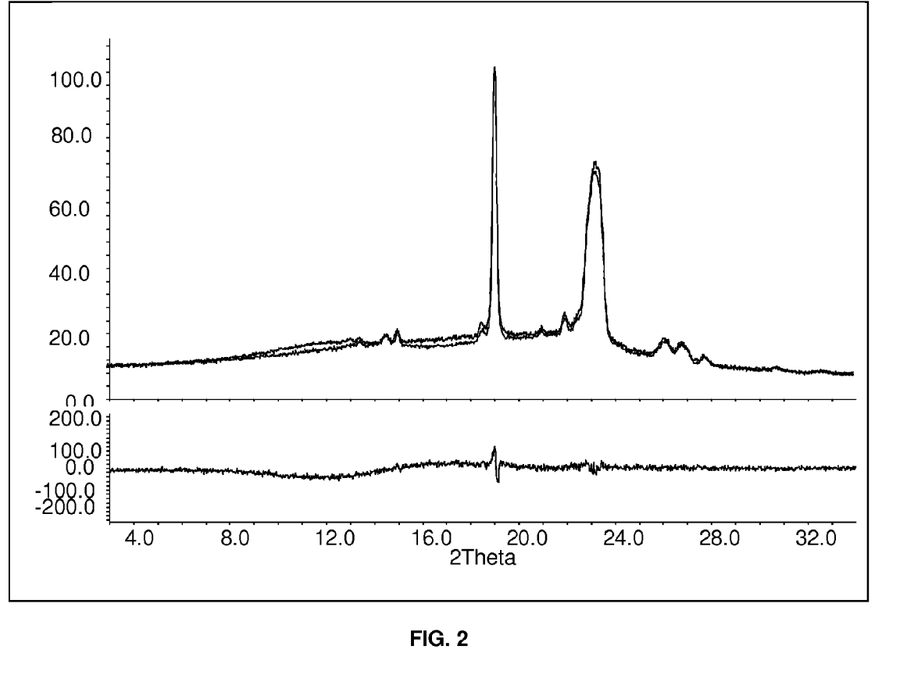
FIG. 2 shows the powder X-ray diffraction pattern of aripiprazole stabilized with polyethylene glycol (Macrogol 6000) and polyvinyl pyrrolidone (Kollidon VA 64) according to example 1, the powder X-ray diffraction pattern of a mixture of polyethylene glycol (Macrogol 6000) and polyvinyl pyrrolidone (Kollidon VA 64) without aripiprazole, and the difference spectrum of the first and second spectrum.

In the upper part of FIG. 2 the spectrum of FIG. 1 is overlaid with the spectrum of a mixture of Macrogol 6000 and Kollidon VA 64 without the active ingredient. In the lower part of FIG. 2 the difference of the two spectra is shown. It can be seen that the peaks of FIG. 1 must be caused by the stabilizing agents, i.e. the aripiprazole contained in the mixture is purely amorphous and does therefore not result in the formation of any additional peaks.

Example 2

Preparation of Stabilized Amorphous Aripiprazole by Mixing the Active Ingredient with Two Stabilizing Agents (Macrogol 6000/Kollidon VA 64) in the Absence of Organic Solvent 5.63 g of polyethylene glycol (Macrogol 6000) and 5.64 g of polyvinyl pyrrolidone (Kollidon VA 64) were heated in a glass vessel to T≈150° C. to 180° C. At that temperature 1.32 g aripiprazole were added with stirring to obtain a homogeneous solution. Stirring was continued for an additional 10 min., then the dispersion was poured into a mortar and allowed to cool down to room temperature.

Example 3

Preparation of Stabilized Amorphous Aripiprazole by Mixing the Active Ingredient with Two Stabilizing Agents (Macrogol 4000/Eudragit EPO)

Figure 3:
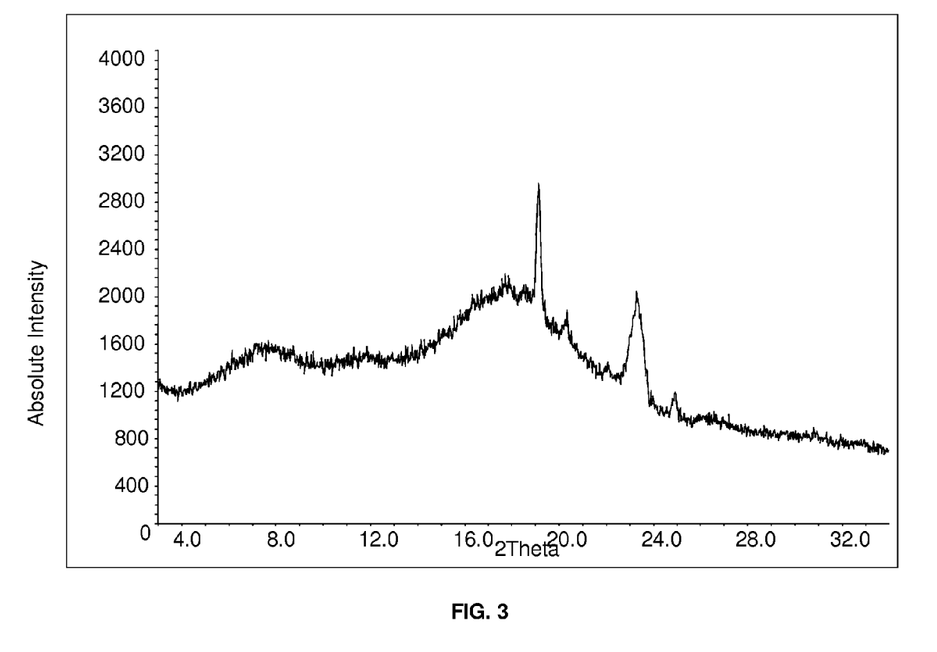
FIG. 3 shows the powder X-ray diffraction pattern of aripiprazole stabilized with polyethylene glycol (Macrogol 4000) and a pH-dependent water soluble polymethacrylate (Eudragit EPO) in the presence of tartaric acid according to Example 3. The observed peaks are due to the crystalline tartaric acid.

1.45 kg of polyethylene glycol (Macrogol 4000), 0.31 kg of Tartaric Acid, 6.79 kg of a pH-dependent water-soluble polymethacrylate (Eudragit EPO) and 1.45 kg of Aripiprazol were mixed and heated in a hot-melt-extruder (Leistritz ZSE-27 HP-40D) to T≈140° C. to 150° C. After the extrusion process the resulting extrudate was allowed to cool down to room temperature and milled. X-ray diffraction measurement of the product resulted in the spectrum shown in FIG. 3.

Example 4

Tablet Containing Stabilized Amorphous Aripiprazole in a Dosage Strength of 10 mg Aripiprazole Tablets of the following composition were prepared by direct compression of mixture of the substances specified in Table I on tabletting machine (Fette P 1200).

| Immediate release tablet | | |
|---|---|---|
| Component | wt.-% | mg per tablet |
| stabilized amorphous aripiprazole (Ex 3) | 34.48 | 68.97[1) |
| Microcrystalline Cellulose | 15.0 | 30.00 |
| Mannitol | 43.52 | 87.03 |
| Crosslinked Polyvinylpyrrolidone | 5.0 | 10.00 |
| Sweeteners | 0.9 | 1.80 |
| Aroma | 0.1 | 0.20 |
| Magnesium stearate | 1.0 | 2.0 |
| Total | 100 | 200.0 |

[1) = 10 mg aripiprazole

Example 5

Dissolution Profile of the Tablets of Example 4 (Batch-No. 74621)

Figure 4:
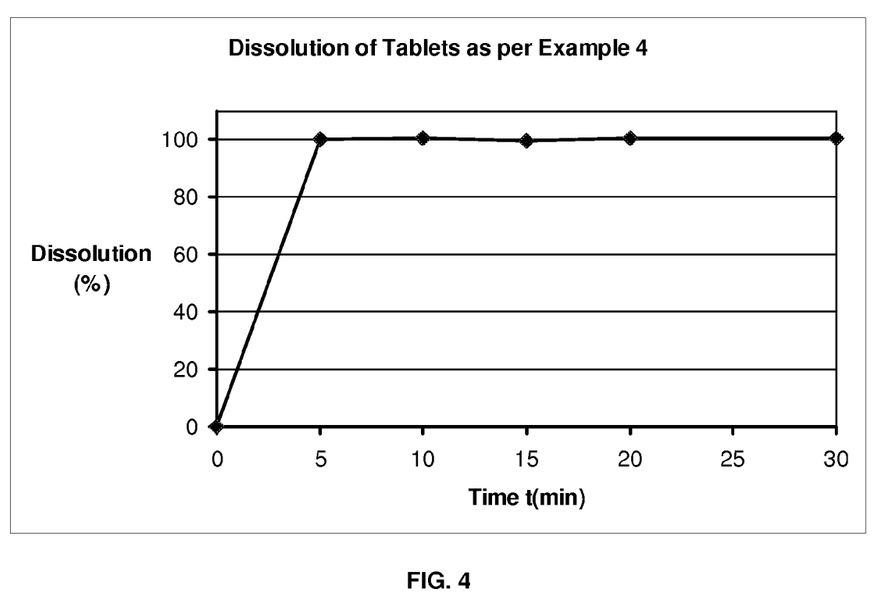
FIG. 4 shows the dissolution profile of the tablets described in example 4.

The dissolution rate of the pharmaceutical composition of example 4 was determined according to USP (900 ml buffer pH 1.2, 37° C., 60 rpm) using an amount of stabilized aripiprazole which corresponds to 10 mg of pure aripiprazole. The dissolution profile is shown in FIG. 4.

Example 6

Results of Biostudy with the Tablets of Example 4 (Batch-No. 74621; Assay 96.4%)

| | Tablets of Example 4 | |
|---|---|---|
| PARAMETER | MEAN | C.V. |
| $C_{max}$ (ng/mL) | 46.26 | 46.5 |
| $T_{max}$ (hours) | 3.17 | 80.5 |
| $AUC_T$ (ng · h/mL) | 1372.86 | 25.2 |
| $AUC_\infty$ (ng · h/mL) | 2477.40 | 29.3 |
| $K_{el}$ (hours$^{-1}$) | 0.0121 | 35.1 |
| $T_{1/2el}$ (hours) | 65.05 | 41.1 |

Figure 5:
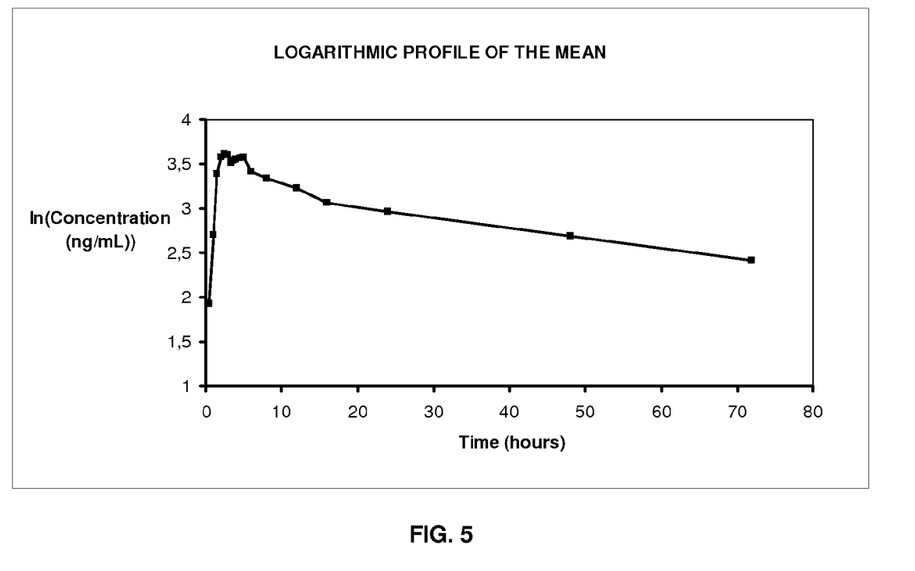
FIG. 5 shows the results of a biostudy with the tablets of example 4 (logarithmic profile of the mean).

The logarithmic profile of the mean is shown in FIG. 5.

Example 7

Tablets Containing Stabilized Amorphous Aripiprazole in Different Dosage Strengths of Aripiprazole

| Component | Dosage strength: 5 mg aripiprazole mg per tablet | Dosage strength: 15 mg aripiprazole mg per tablet | Dosage strength: 20 mg aripiprazole mg per tablet | Dosage strength: 30 mg aripiprazole mg per tablet |
|---|---|---|---|---|
| stabilized amorphous aripiprazole of example 3 | 34.49 | 103.45 | 137.94 | 206.91 |
| Microcrystalline Cellulose | 15.00 | 45.00 | 60.00 | 90.00 |
| Mannitol | 43.51 | 130.55 | 174.06 | 261.09 |
| Crosslinked Polyvinylpyrrolidone | 5.00 | 15.00 | 20.00 | 30.00 |
| Sweeteners | 0.90 | 2.70 | 3.60 | 5.40 |
| Aroma | 0.10 | 0.30 | 0.40 | 0.60 |
| Magnesium stearate | 1.0 | 3.0 | 4.0 | 6.0 |
| Total | 100.0 | 300.0 | 400.0 | 600.0 |

The invention claimed is:

1. Morphologically stabilized amorphous aripiprazole.
2. A composition comprising amorphous aripiprazole and at least one stabilizing agent.
3. The composition of claim 2, comprising
    a first stabilizing agent selected from the group consisting of polyvinyl pyrrolidone, polymethylacrylate, polyvinyl acetate phthalate, alkyl cellulose, hydroxyalkyl cellulose, derivatives of these substances, and mixtures thereof, and
    a second stabilizing agent selected from the group consisting of polyethylene glycol, polyoxyethylene castor oil, polyoxyethylene hydrogenated castor oil, polyethylene glycol sorbitan fatty acid, polyethylene polypropylene glycol, polyethylene oxide, polyoxyethylene alkyl ether, polyoxyethylene stearate, derivatives of these substances, and mixtures thereof.
4. The composition of claim 3 wherein said first stabilizing agent is a polymethacrylate and said second stabilizing agent a polyethylene glycol.
5. The composition of claim 4, wherein the polymethacrylate is a pH-dependent water-soluble polymethacrylate.
6. The composition of claim 5, wherein the polymethacrylate is a dimethyl aminoethyl methacrylate copolymer.
7. The composition of claim 3, wherein the polyethylene glycol is a polyethylene glycol having an average molecular weight within the range of 190 to 10,000.
8. The composition of claim 3, comprising the first stabilizing agent and the second stabilizing agent in a weight ratio of 5:1 to 1:5.
9. The composition of claim 2, comprising 4.8 to 83.3 wt.-% of aripiprazole.
10. The composition of claim 2, comprising 3.8 to 66.7 wt.-% of amorphous aripiprazole.
11. A process for preparing morphologically stabilized amorphous aripiprazole comprising the mixing of aripiprazole with a stabilizing agent or mixture of stabilizing agents.
12. The process of claim 11 wherein the aripiprazole is dissolved in a mixture of
    a first stabilizing agent selected from the group consisting of polyvinyl pyrrolidone, polymethylacrylate, polyvinyl acetate phthalate, alkyl cellulose, hydroxyl alkyl cellulose, and derivatives and/or a mixture thereof, and
    a second stabilizing agent selected from the group consisting of polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, and derivatives and/or a mixture thereof.
13. The process of claim 12, wherein the aripiprazole is dissolved in a mixture of at least a polymethacrylate as first stabilizing agent and a polyethylene glycol as second stabilizing agent.
14. The process of claim 12, wherein the aripiprazole and stabilizing agent(s) are used in a weight ratio of 1:20 to 5:1.
15. The process of claim 12, wherein the first stabilizing agent and the second stabilizing agent are used in a weight ratio of 5:1 to 1:5.
16. The process of claim 12, wherein aripiprazole, first and second stabilizing agent are used in a weight ratio of 1:10:10 to 1:0.5:0.5.
17. The process of claim 12, wherein the mixture is heated at a temperature of 40 to 190° C.
18. The process of claim 17, wherein the active ingredient and the stabilizing agents are mixed and heated in an extruder, followed by extrusion of the mixture.
19. A composition comprising morphologically stabilized amorphous aripiprazole obtainable according to a process of claim 12.
20. A method for converting crystalline aripiprazole to morphologically stabilized amorphous aripiprazole said method comprising combining crystalline aripiprazole with at least two different stabilizing agents.
21. A pharmaceutical composition comprising a composition of claim 2, and at least one pharmaceutically acceptable excipient.
22. The pharmaceutical composition of claim 21, comprising 1 to 99.5 wt.-% of morphologically stabilized amorphous aripiprazole, containing 0.1 to 95 wt.-% of stabilizing agent(s).
23. The pharmaceutical composition of claim 21, comprising:
    1 to 99.5 wt.-% morphologically stabilized amorphous aripiprazole, and 0.5 to 99 wt.-% further excipients.
24. The pharmaceutical composition of claim 21, comprising:
    1 to 99 wt.-% of morphologically stabilized amorphous aripiprazole,
    0.5 to 50 wt.-% disintegration aids, and
    0.5 to 90 wt.-% filler.
25. The pharmaceutical composition of claim 24, further comprising:
    0.1 to 10 wt.-% lubricant, and
    0 to 5 wt.-% flavor.
26. The pharmaceutical composition of claim 21 having a bioavailability with an average $c_{max}$ larger than 25 ng/ml of aripiprazole, an average $t_{max}$ below 4 hours and an average $AUC_\infty$ larger than 1500 ng·h/ml.
27. A method for the manufacture of an oral pharmaceutical formulation selected from flash-melt tablets, oral dispersible tablets, sustained release tablets, said method comprising combining the composition of claim 2 with at least one pharmaceutically acceptable excipient.
28. The method of claim 20, said method comprising combining crystalline aripiprazole with at least
    a first stabilizing agent selected from the group consisting of polyvinyl pyrrolidone, polymethylacrylate, polyvinyl acetate phthalate, alkyl cellulose, hydroxyl alkyl cellulose, and derivatives and/or a mixture thereof, and
    a second stabilizing agent selected from the group consisting of polyethylene glycol, polyoxyethylene castor oil, polyethylene glycol sorbitan fatty acid, polyethylene polypropylene glycol, polyethylene oxide, polyoxyethylene alkyl ether, polyoxyethylene stearate, and derivatives and/or a mixture thereof.
29. The method of claim 27, wherein the at least one pharmaceutically acceptable excipient is selected from the group consisting of fillers, lubricants, disintegration aids, wetting agents, agents to improve the flow behavior, antioxidants, flavors, taste masking agents, pigments and dyes.

* * * * *